US006261224B1

(12) United States Patent
Adams et al.

(10) Patent No.: US 6,261,224 B1
(45) Date of Patent: Jul. 17, 2001

(54) PIEZOELECTRIC FILM TRANSDUCER FOR COCHLEAR PROSTHETIC

(75) Inventors: Theodore P. Adams, Edina; Bruce A. Brillhart, Stillwater; Donald J. Bushek, Plymouth; Kai Kroll, Minnetonka, all of MN (US)

(73) Assignee: St. Croix Medical, Inc., Minneapolis, MN (US)

( * ) Notice: Subject to any disclaimer, the term of this patent is extended or adjusted under 35 U.S.C. 154(b) by 0 days.

(21) Appl. No.: 09/304,327

(22) Filed: May 3, 1999

Related U.S. Application Data

(63) Continuation of application No. 08/908,243, filed on Aug. 7, 1997, now Pat. No. 5,899,847, which is a continuation-in-part of application No. 08/689,312, filed on Aug. 7, 1996, now Pat. No. 5,762,583.

(51) Int. Cl.[7] .................................................. H04R 25/00
(52) U.S. Cl. ............................................. 600/25; 607/57
(58) Field of Search .......................... 607/55–57; 600/25

(56) References Cited

U.S. PATENT DOCUMENTS

| 3,557,775 | 1/1971 | Mahoney ................................ 128/1 |
| 3,594,514 | 7/1971 | Wingrove ........................ 179/107 R |
| 3,712,962 | 1/1973 | Epley ............................... 179/107 R |

(List continued on next page.)

FOREIGN PATENT DOCUMENTS

| 4104358 A1 | 2/1991 | (DE) | ............................. H04R/25/02 |
| 4221866 A1 | 1/1994 | (DE) | .................................... 381/312 |
| 19618961A1 | 5/1996 | (DE) | .................................... 600/559 |
| 19638158A1 | 9/1996 | (DE) | ............................. A16B/1/375 |
| 19638159A1 | 9/1996 | (DE) | ............................. H04R/25/02 |
| 19618329A1 | 11/1997 | (DE) | ............................. B29C/51/12 |
| 0 537 026 A2 | 4/1993 | (EP) | .................................... 381/312 |

OTHER PUBLICATIONS

Dormer, Phd., K.J., et al. "Selection of Biomaterials for Middle and Inner Ear Implants, " Otolaryngologic Clinics of North America, 28:17–28, (1995).

Frederickson, M. D., J. M., et al., "Ongoing Investigations into an Implantable Electromagnetic Hearing Aid for Moderate to Severe Sensorineural Hearing Loss, " Otolaryngologic Clinics of North America, 28:107–120, (1995).

Gyo, K., et al., "Staples Vibration Produced by the Output Transducer of an Implantable Hearing Aid,"Archives of Otolaryngology Head and Neck Surgery, 1113:1078–1081, (1987).

Gyo, K., et al., "Sound Pickup Utilizing an Implantable Piezoelectric Ceramic Bimorph Element: Application to the Cochlear Implant," American Journal of Otology 5:273–276, (1984).

Jako, M.D., G. J., "biomedical Engineering in Ear Surgery," Otolaryngologi Clinics of North America, 5:173–182, (1972).

Ko, Phd., W., "Engineering Principles of Mechanical Stimulation of the Middle Ear," Otolaryngologic Clinics of North America, 28:29–41, (1995).

(List continued on next page.)

*Primary Examiner*—Carl H. Layno
(74) *Attorney, Agent, or Firm*—Fredrikson & Byron, P.A.

(57) ABSTRACT

A method and apparatus transduces between mechanical and electrical signals within a middle ear to improve hearing. An electromechanical transducer film, preferably polyvinylidene fluoride (PVDF), is carried by a mount secured to the middle ear. The film is constrained by the mount, or by the mount and an auditory element. The invention includes substantially straight, bow-shaped, hoop-shaped, and bi-element transducer film embodiments. The film transduces between mechanical vibrations of an auditory element, such as the malleus or stapes, and electrical signals for use with an electronics unit of a partial middle ear implantable (P-MEI) or total middle ear implantable (T-MEI) hearing aid.

43 Claims, 11 Drawing Sheets

U.S. PATENT DOCUMENTS

| | | | |
|---|---|---|---|
| 3,764,748 | 10/1973 | Branch et al. | 179/107 E |
| 3,931,648 | 1/1976 | Shea, Jr. | 3/1.9 |
| 3,943,614 | 3/1976 | Yoshikawa, et al. | 29/25.35 |
| 3,970,862 | 7/1976 | Edelman, et al. | 307/88 |
| 4,204,135 | 5/1980 | Murayama | 310/357 |
| 4,316,115 | 2/1982 | Wilson, et al, | 310/327 |
| 4,330,730 | 5/1982 | Kurz et al. | 310/331 |
| 4,369,391 | 1/1983 | Micheron | 310/800 |
| 4,729,366 * | 3/1988 | Schaefer | 607/57 |
| 4,774,933 | 10/1988 | Hough, et al. | 600/25 |
| 4,776,322 | 10/1988 | Hough, et al. | 128/1.6 |
| 4,817,607 | 4/1989 | Tatge | 128/419 R |
| 4,840,178 | 6/1989 | Heide, et al. | 128/419 R |
| 4,850,962 | 7/1989 | Schaefer | 600/25 |
| 4,957,478 | 9/1990 | Maniglia | 600/25 |
| 5,012,520 * | 4/1991 | Steeger | 600/25 |
| 5,015,224 | 5/1991 | Magniglia | 600/25 |
| 5,015,225 | 5/1991 | Hough et al. | 600/25 |
| 5,163,957 | 11/1992 | Sadé | 623/10 |
| 5,277,694 | 1/1994 | Leysieffer, et al. | 600/25 |
| 5,282,858 | 2/1994 | Bisch et al. | 364/514 |
| 5,311,449 | 5/1994 | Adams | 364/514 |
| 5,338,287 | 8/1994 | Miller, et al. | 600/25 |
| 5,344,387 | 9/1994 | Lupin | 600/25 |
| 5,360,388 | 11/1994 | Spindel et al. | 600/25 |
| 5,383,915 | 1/1995 | Adams | 607/60 |
| 5,411,467 | 5/1995 | Hortmann et al. | 600/25 |
| 5,456,654 | 10/1995 | Ball | 600/25 |
| 5,498,226 * | 3/1996 | Lenkauskas | 600/25 |
| 5,531,787 | 7/1996 | Lesinski et al. | 623/10 |
| 5,554,096 | 9/1996 | Ball | 600/25 |
| 5,624,376 | 4/1997 | Ball et al. | 600/25 |
| 5,762,583 | 6/1998 | Adams et al. | 600/25 |
| 5,800,336 | 9/1998 | Ball et al. | 600/25 |
| 6,140,740 | 10/2000 | Porat et al. | 310/322 |

OTHER PUBLICATIONS

Kodera, M.D. K., et al. "Sound Evaluation of Partially Implantable Piezoelectric Middle Ear Implant: Comparative Study of Frequency Responses, " Ear Nose and Throat Journal, 73:108–111, (1994).

Tjellström, M.D., PhD., A., "The Bone–Anchored Hearing Aid," Otolaryngologic Clinics of North America, 28:53–72, (1995).

Maniglia, M.D., A.J., "A Contactless Electromagnetic Implantable Middle Ear Device for Sensorineural Hearing Loss, " Ear, Nose and Throat Journal, 73(2), (1994).

Suzuki, J. I., et al., "Long–Term Clinical Results of the Partially Implantable Middle Ear Implant," Ear, Nose and Throat Journal, 73(2): 104–107, (Feb 1994).

Tos, M., et al., "Implantation of Electromagnetic Ossicular Replacement Device," Ear, Nose and Throat Journal, 73(2):93–103, (Feb 1994).

* cited by examiner

PIEZOELECTRIC FILM TRANSDUCER FOR COCHLEAR PROSTHETIC

This application is a continuation of U.S. patent application Ser. No. 08/908,243, filed Aug. 7, 1997, now U.S. Pat. No. 5,899,847, and entitled, "PIEZOELECTRIC FILM TRANSDUCER," which is a continuation-in-part of U.S. Patent application Ser. No. 08/689,312, filed Aug. 7, 1996, now U.S. Pat. No. 5,762,583, issued Jun. 9, 1998.

THE FIELD OF THE INVENTION

This invention relates to an electromechanical transducer for use in a hearing system implantable in a middle ear.

BACKGROUND

In some types of partial middle ear implantable (P-MEI) or total middle ear implantable (T-MEI) hearing aid systems, sounds produce mechanical vibrations which are transduced by an electromechanical input transducer into electrical signals. These electrical signals are in turn amplified and applied to an electromechanical output transducer. The electromechanical output transducer vibrates an ossicular bone in response to the applied amplified electrical signals, thereby improving hearing.

Such electromechanical input and output transducers should be proportioned to provide convenient implantation in the middle ear. Low power consumption transducers are also desired for use with a limited longevity implanted battery as a power source. The electromechanical input transducer should have high sensitivity, gain, linearity, and a wide dynamic range in producing electrical signals from a sensed mechanical vibration. The electromechanical output transducer should have low power consumption in producing mechanical vibrations from an applied electrical input signal.

SUMMARY OF THE INVENTION

The invention provides a piezoelectric transducer film disposed within the middle ear and a method of use, such as with a middle ear implantable (MEI) hearing system including a partial middle ear implantable (P-MEI) hearing aid system or a total middle ear implantable (T-MEI) hearing aid system.

In one embodiment, the invention is used as an electromechanical output transducer. A mount carrying a piezoelectric transducer film is secured to the middle ear. An electrical input signal is applied to the film to dynamically vary the film length. The film is constrained such that variations in the film length produce positional film variations which are mechanically coupled to vibrate an auditory element.

In one embodiment, as an electromechanical output transducer, the film is mechanically coupled to first and second constraint points, such as on the mount, or on the mount and on the auditory element. The film is optionally bowed away from the mount. A variation in film length between the first and second constraint points is transformed into a positional variation of a driving point of the film. The driving point of the film couples mechanical vibrations to an auditory element such as the stapes.

In another embodiment, a hoop-shaped piezoelectric electromechanical output transducer film (hoop) is mechanically coupled to the mount at a coupling point. The hoop is coupled to first and second constraint points on first and second arms extending radially outward from the mount. An applied electrical input signal causes variations in a circumferential length of the hoop. The variations in the circumferential length of the hoop are transformed into positional variations that are typically approximately orthogonal to a longitudinal direction of the mount as a result of constraining by the first and second arms. The positional variations couple mechanical vibrations to an auditory element such as the stapes.

In another embodiment, the invention is used as an electromechanical input transducer. A mount carrying a piezoelectric transducer film is secured to the middle ear. The film is coupled to an auditory element, such as the malleus, for receiving mechanical vibrations resulting from sound waves. The film transducer produces an output voltage in response to the mechanical vibrations. The film is mechanically coupled to first and second constraint points, such as on the mount, or on the mount and on the auditory element.

In one embodiment, as an electromechanical input transducer, the film is mechanically coupled to the mount at first and second constraint points. The film is optionally bowed away from the mount. The film is coupled to an auditory element, such as the malleus, at a vibrated point between the first and second constraint points. Received vibrations constrain the length of the film, producing an electrical output signal in response.

In another embodiment, as an electromechanical input transducer, a hoop-shaped film is mechanically coupled to the mount at a coupling point. The film is coupled to first and second constraint points on first and second arms extending radially outward from the mount. A vibrated point on the film is coupled to an auditory element, such as the malleus. Received vibrations constrain the circumferential length of the film, producing a resulting electrical output signal in response.

Thus, the invention includes an electromechanical input transducer film receiving mechanical vibrations from an auditory element and providing a resulting electrical signal to an electronics unit of an implantable hearing system. The invention also includes an electromechanical output transducer film receiving electrical signals from the electronics unit of an implantable hearing system and vibrating an auditory element in response. The invention also provides an electronics unit and a programmer.

BRIEF DESCRIPTION OF THE DRAWINGS

In the drawings, like numerals describe like components throughout the several views.

DETAILED DESCRIPTION

Figure 1:
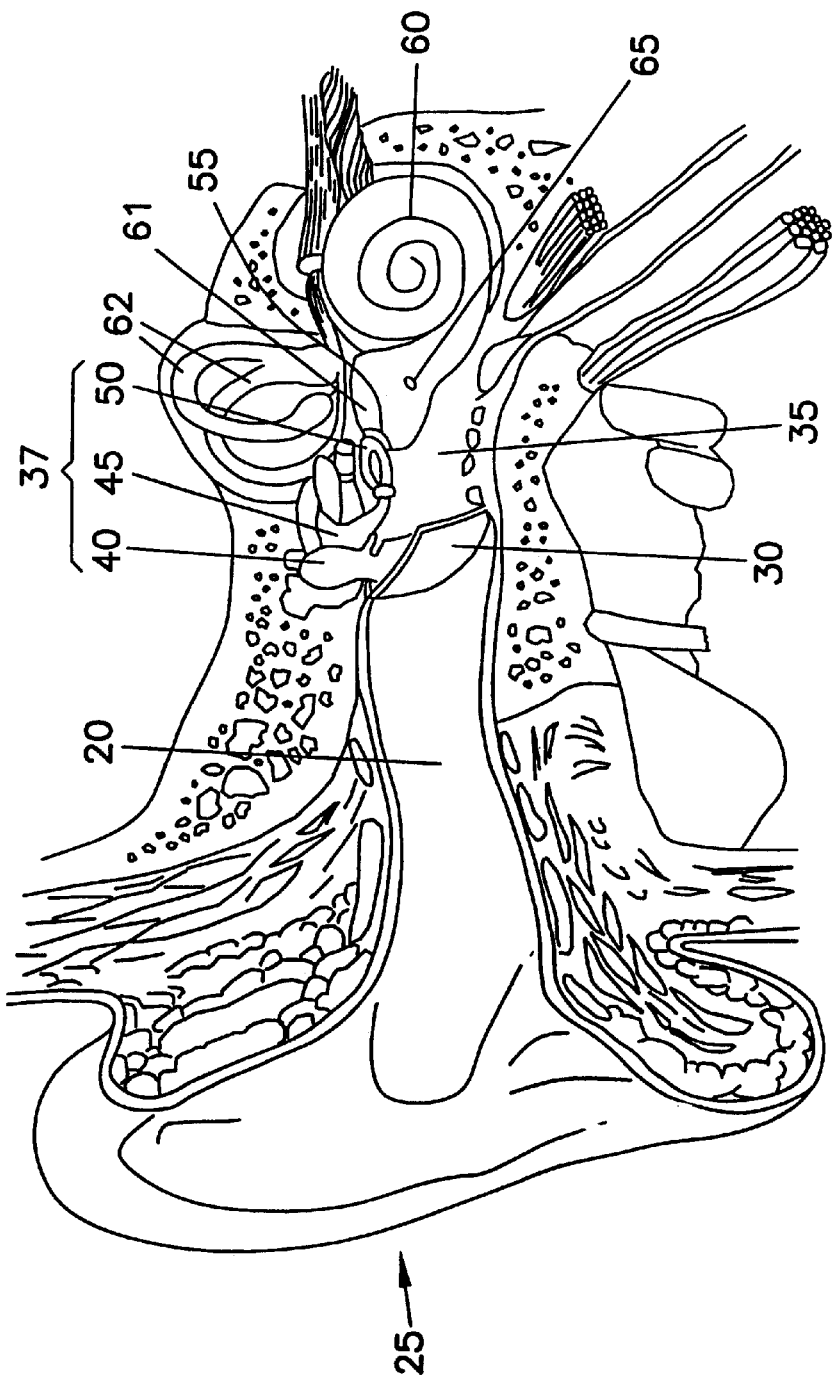
FIG. 1 illustrates a frontal section of an anatomically normal human right ear in which the invention operates.

The invention provides an electromechanical transducer which is particularly advantageous when used in a middle ear implantable hearing system such as a partial middle ear implantable (P-MEI), total middle ear implantable (T-MEI), or other hearing aid system. A P-MEI or T-MEI hearing aid system assists the human auditory system in converting acoustic energy contained within sound waves into electrochemical signals delivered to the brain and interpreted as sound. FIG. 1 illustrates generally the use of the invention in a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three primary components: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing aid systems have also been developed, utilizing various approaches to compensate for hearing disorders. For example, cochlear implant techniques implement an inner ear hearing aid system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing aid systems have been developed to aid patients without an intact tympanic membrane 30, upon which "air conduction" hearing aids depend. For example, temporal bone conduction hearing aid systems produce mechanical vibrations that are coupled to the cochlea 60 via a temporal bone in the skull. In such temporal bone conduction hearing aid systems, a vibrating element can be implemented percutaneously or subcutaneously.

A particularly interesting class of hearing aid systems includes those which are configured for disposition principally within the middle ear 35 space. In middle ear implantable (MEI) hearing aids, an electrical-to-mechanical output transducer couples mechanical vibrations to the ossicular chain 37, which is optionally interrupted to allow coupling of the mechanical vibrations to the ossicular chain 37. Both electromagnetic and piezoelectric output transducers have been used to effect the mechanical vibrations upon the ossicular chain 37.

One example of a partial middle ear implantable (P-MEI) hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption, which limits their usefulness in total middle ear implantable (T-MEI) hearing aid systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

Piezoelectric output transducers have several advantages over electromagnetic output transducers. The smaller size or volume of the piezoelectric output transducer advantageously eases implantation into the middle ear 35. The lower power consumption of the piezoelectric output transducer is particularly attractive for T-MEI hearing aid systems, which include a limited longevity implanted battery as a power source. The invention provides an piezoelectric electromechanical input/output transducer for disposition within middle ear 35 and for use with a P-MEI, T-MEI, or hearing system.

Figure 2:
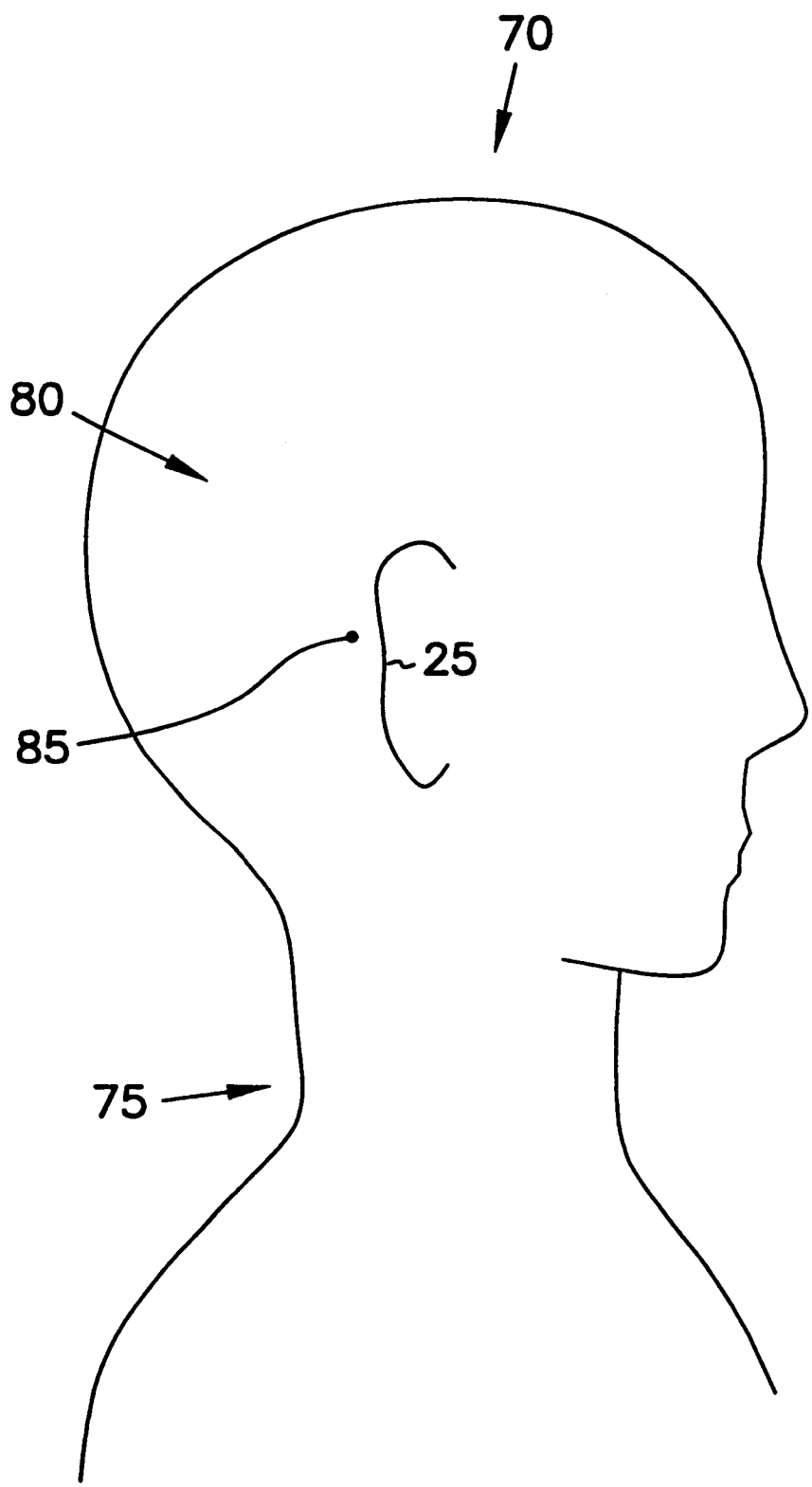
FIG. 2 is a schematic illustration of the right side of a person's head and neck regions.

FIG. 2 is a schematic diagram illustrating a view of the right side of a person's head 70 and neck 75. Outer ear 25 is slightly pulled anteriorly, to expose a region of the temporal bone known as the mastoid 80. An incision is made in the skin covering the mastoid 80, and an underlying access hole 85 is created through the mastoid 80, allowing external access to the middle ear 35. The access hole 85 is located approximately posterior and superior to the external auditory canal 20. By placing the access hole 85 in this region, a transducer is disposed within the middle ear 35 cavity.

Figure 3:
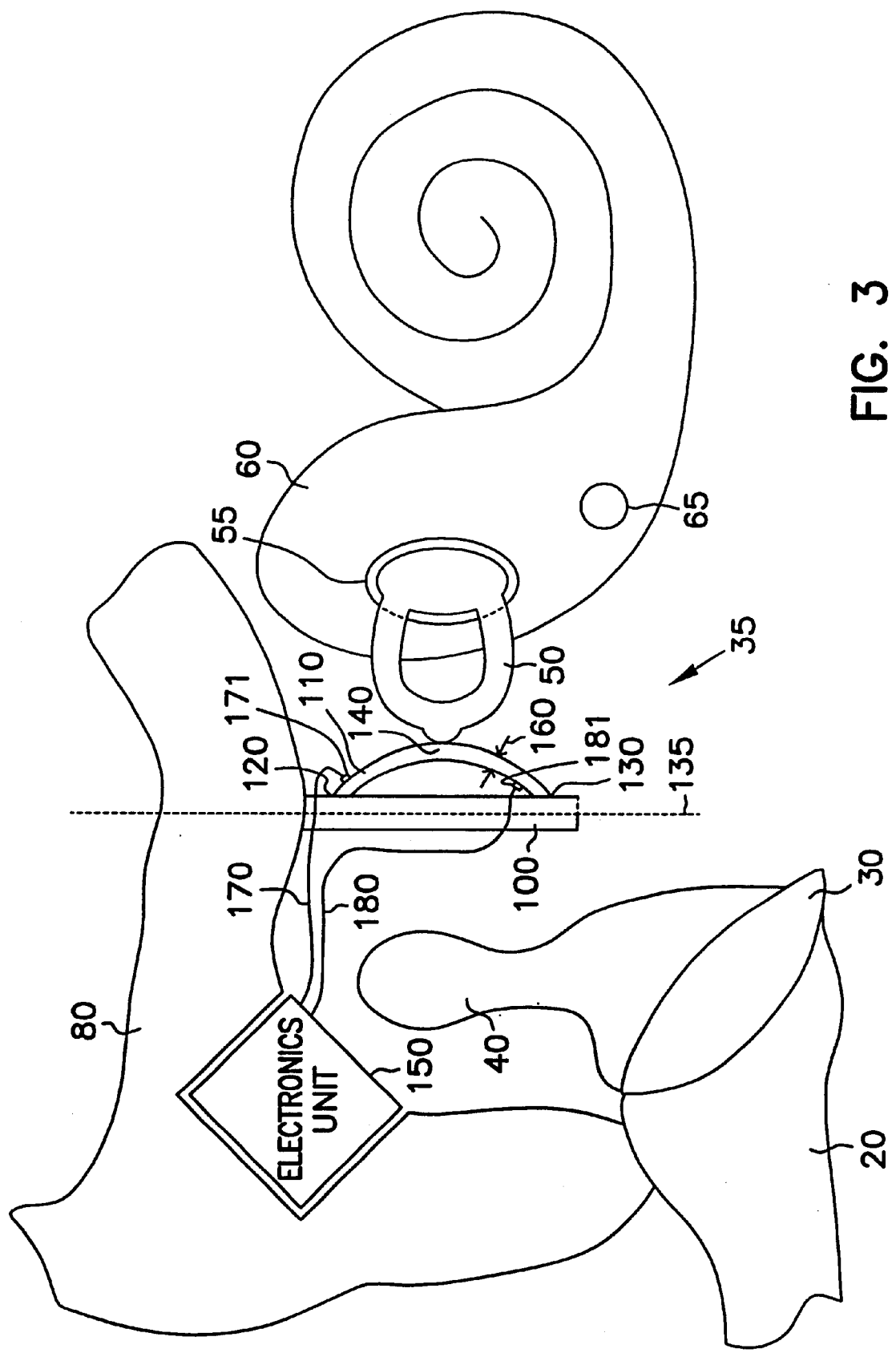
FIG. 3 is a schematic illustration of one embodiment of the invention having a bow-shaped piezoelectric output transducer film.

FIG. 3 illustrates middle ear 35 in more detail, in which one embodiment of the invention is used as an electromechanical output transducer. FIG. 3 includes external auditory canal 20, tympanic membrane 30, malleus 40, stapes 50, oval window 55, cochlea 60, and a portion of mastoid 80. Incus 45 has been removed, though this is not required for operation of the invention. A mount 100 is cantilevered from its proximal end, which is secured to mastoid 80. A distal end of mount 100 extends longitudinally from the proximal end of mount 100 into middle ear 35. Mount 100 comprises any rigid biocompatible material. Examples of biocompatible materials include titanium, stainless steel, certain ceramics (e.g. alumina), certain polymers (e.g. tetrafluoropolyethylene, sold under the trade name "Teflon"), and other materials well known to one skilled in the art. Mount 100 is secured to mastoid 80 by any known attachment technique. Examples of attachment techniques include a self-tapping portion of mount 100, a lip portion extending radially from the proximal portion of mount 100 for receiving a bone screw or other fastener and securing mount 100 to mastoid 80, a biocompatible adhesive attachment, a receiving indentation in mastoid 80, or another attachment technique known to one skilled in the art.

In FIG. 3, a piezoelectric transducer film 110 is carried by mount 100. Film 10 is secured to mount 100 at a first constraint point 120 at the proximal end of mount 100 and is also secured to mount 100 at a second constraint point 130 at the distal end of mount 100. The direct distance between the first and second constraint points 120 and 130 is in a longitudinal direction 135 of mount 100. Film 110 is bowed away from mount 100 between the first and second constraint points 120 and 130. The distance between first and second constraint points 120 and 130 along the bowed surface of film 110 defines a length of the film 110. A driving point 140 of film 110, intermediate between the first and second constraint points 120 and 130, is mechanically coupled within middle ear 35 to an auditory element, such as the head portion of stapes 50. In one embodiment driving point 140 is adhesively affixed to the head portion of stapes 50. Film 10 is secured to mount 100 at the first and second constraint points 120 and 130 by any suitable technique such as by a mechanical fastener, by an adhesive, or by forming receptacles in mount 100 at first and second constraint points 120 and 130 for receiving and constraining film 110 such that the film 110 is under tension and held in place by the receptacles.

In FIG. 3, film 110 is a highly piezoelectric film such as a polarized fluoropolymer, e.g. polyvinylidene fluoride (PVDF). For this application, a PVDF film such as that sold under the trademark "Kynar" by AMP, Inc., of Harrisburg, Pa., is the preferred material for film 110. Film 110 receives an electrical input signal, representing transduced sounds, from an electronics unit 150 implanted in a cavity of mastoid 80 as part of a MEI hearing system. The electronics unit 150 couples the electronic input signal across a thickness 160 of film 110 through its output leads 170 and 180 to respective connection points 171 and 181, located across thickness 160 of film 110 at any convenient points. Alternating polarities of the applied electrical input signal cause variations in the length of film 110. Film 110 is mechanically coupled to stapes 50 to define the location of a driving point 140, which is approximately midway between first and second constraint points 120 and 130 or selectably located elsewhere on film 110. Film 110 is optionally also affixed to stapes 50 at driving point 140.

By constraining the film 110 at first and second constraint points 120 and 130, driving point 140 is deflected toward and away from mount 100 when the length of film 110 decreases and increases respectively. Thus, variations in the length of film 110 are transformed into positional variations of driving point 140 that are typically approximately orthogonal to the longitudinal direction 135 of mount 100. Forces resulting from the positional variations of driving point 140 are mechanically coupled to the head portion of stapes 50, causing mechanical vibrations of stapes 50, which are transmitted to cochlea 60 at oval window 55.

Figure 4:
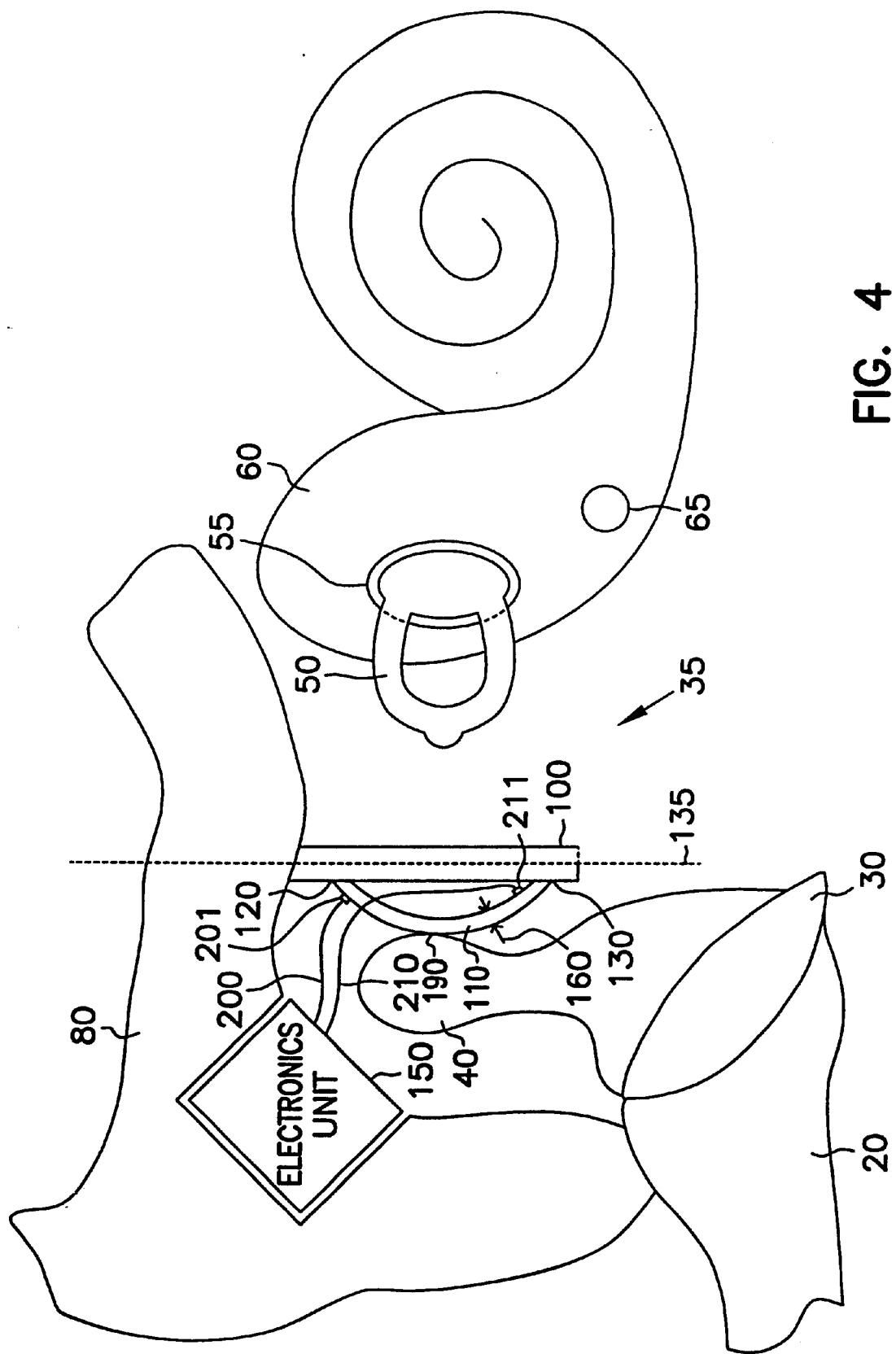
FIG. 4 is a schematic illustration of another embodiment of the invention having a bow-shaped piezoelectric input transducer film.

FIG. 4 illustrates an electromechanical input transducer embodiment of the invention. Film 10 is bowed away from mount 100 toward malleus 40. Film 110 is mechanically coupled, and optionally affixed, to malleus 40 to define a vibrated point 190, which is approximately intermediate on film 110 between first and second constraints 120 and 130, or selectably located elsewhere on film 110. Sounds received at tympanic membrane 30 cause vibrations in malleus 40, which in turn cause positional variations in vibrated point 190 that are typically approximately orthogonal to the longitudinal direction 135 of mount 100. Forces resulting from the positional variations in vibrated point 190 impart a stress in the length of film 110, which in turn produces a resulting electrical output signal across thickness 160 of film 110. The electrical output signal across thickness 160 of film 110 is provided to electronics unit 150 at connection points 201 and 211, located across thickness 160 of film 110 at any convenient points, to respective input leads 200 and 210.

Figure 5:
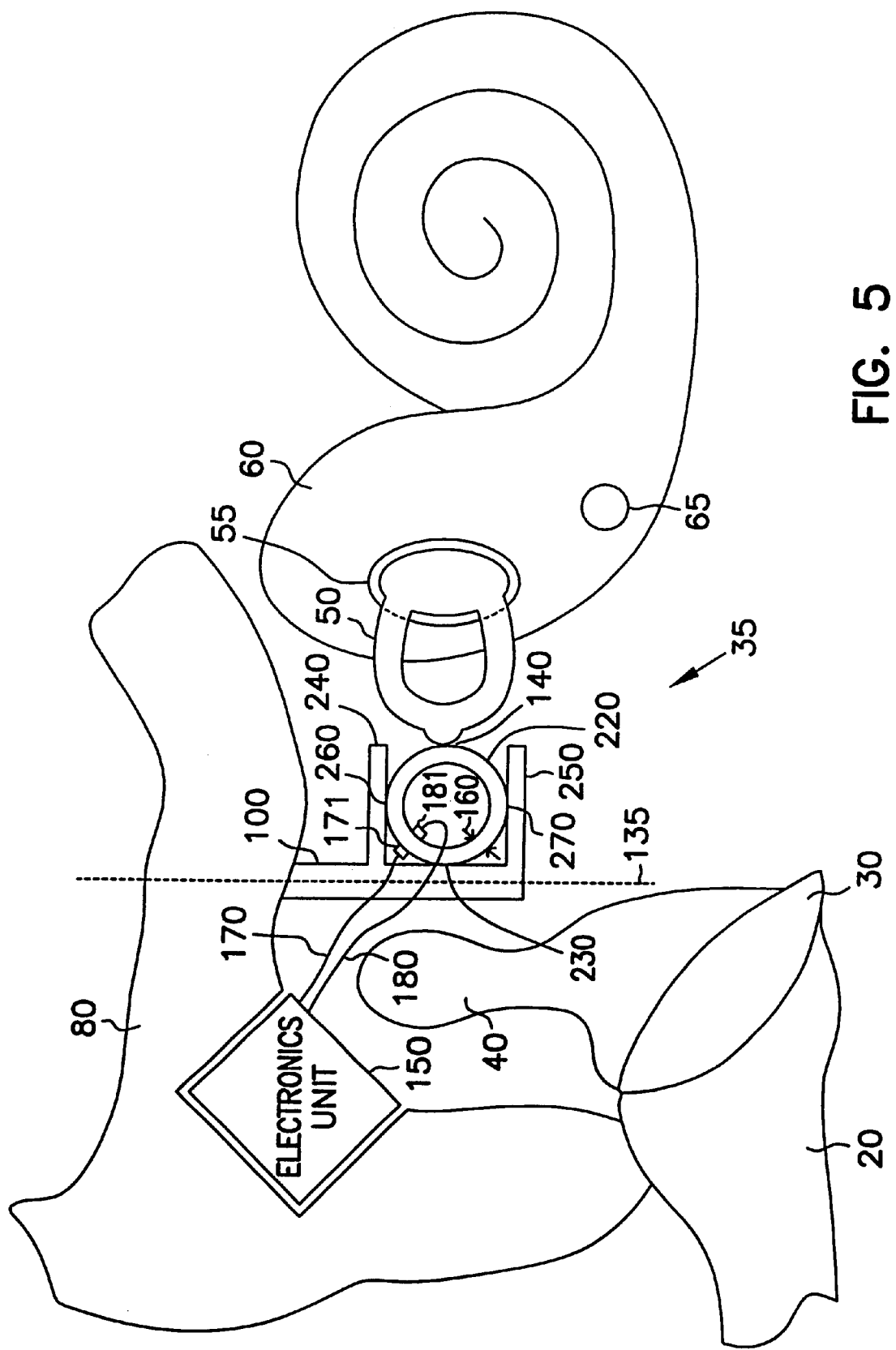
FIG. 5 is a schematic illustration of another embodiment of the invention having a hoop-shaped piezoelectric output transducer film.

FIG. 5 illustrates an electromechanical output transducer embodiment of the invention in middle ear 35. Hoop-shaped piezoelectric transducer film 220 is carried by mount 100. Film 220 is interposed between mount 100 and stapes 50. Film 220 comprises the same material described above with respect to film 110. Film 220 is mechanically coupled to mount 100 at a coupling point 230, and preferably secured by a mechanical fastener, biocompatible adhesive attachment, or equivalent technique. First and second arms 240 and 250 each extend outward radially from mount 100. First and second arms 240 and 250 mechanically constrain, and are optionally secured, to film 220 at respective first and second constraint points 260 and 270. A circumferential distance along the hoop-shaped inner surface of film 220 defines a circumferential length of film 220. Film 220 is mechanically coupled, and optionally affixed, to stapes 50 to define the location of driving point 140, which is approximately intermediate on film 220 between first and second constraints 260 and 270, or selectably located elsewhere along the circumference of film 220.

In FIG. 5, film 220 receives an electrical input signal, representing transduced sounds, from an electronics unit 150 implanted in a cavity of mastoid 80 as part of a MEI hearing system. Electronics unit 150 applies the electrical input signal at electronics unit 150 through its output leads 170 and 180 to connection points 171 and 181, respectively located across the thickness 160 of the film 220 at any convenient points. Alternating polarities of the applied electrical input signal cause variations in the circumferential length of film 220. By constraining film 220 at first and second constraint points 260 and 270, driving point 140 is deflected toward and away from mount 100 when the circumferential length of film 220 decreases and increases respectively. Thus, variations in the circumferential length of film 220 are deflected into positional variations of driving point 140 that are typically approximately orthogonal to the longitudinal direction 135 of mount 100. Forces resulting from the positional variations of driving point 140 are mechanically coupled to the head portion of stapes 50, causing mechanical vibrations of stapes 50, which are transmitted to cochlea 60 at oval window 55. If the circumferential length of the hoop-shaped film 220 of FIG. 5 exceeds the length of the bow-shaped film 110 of FIG. 3, and film 110 is not secured at first and second constraint points 260 and 270, a larger positional variation in driving point 140 will result in the embodiment of FIG. 5 for the same fractional change in length produced by the applied electrical signal.

Figure 6:
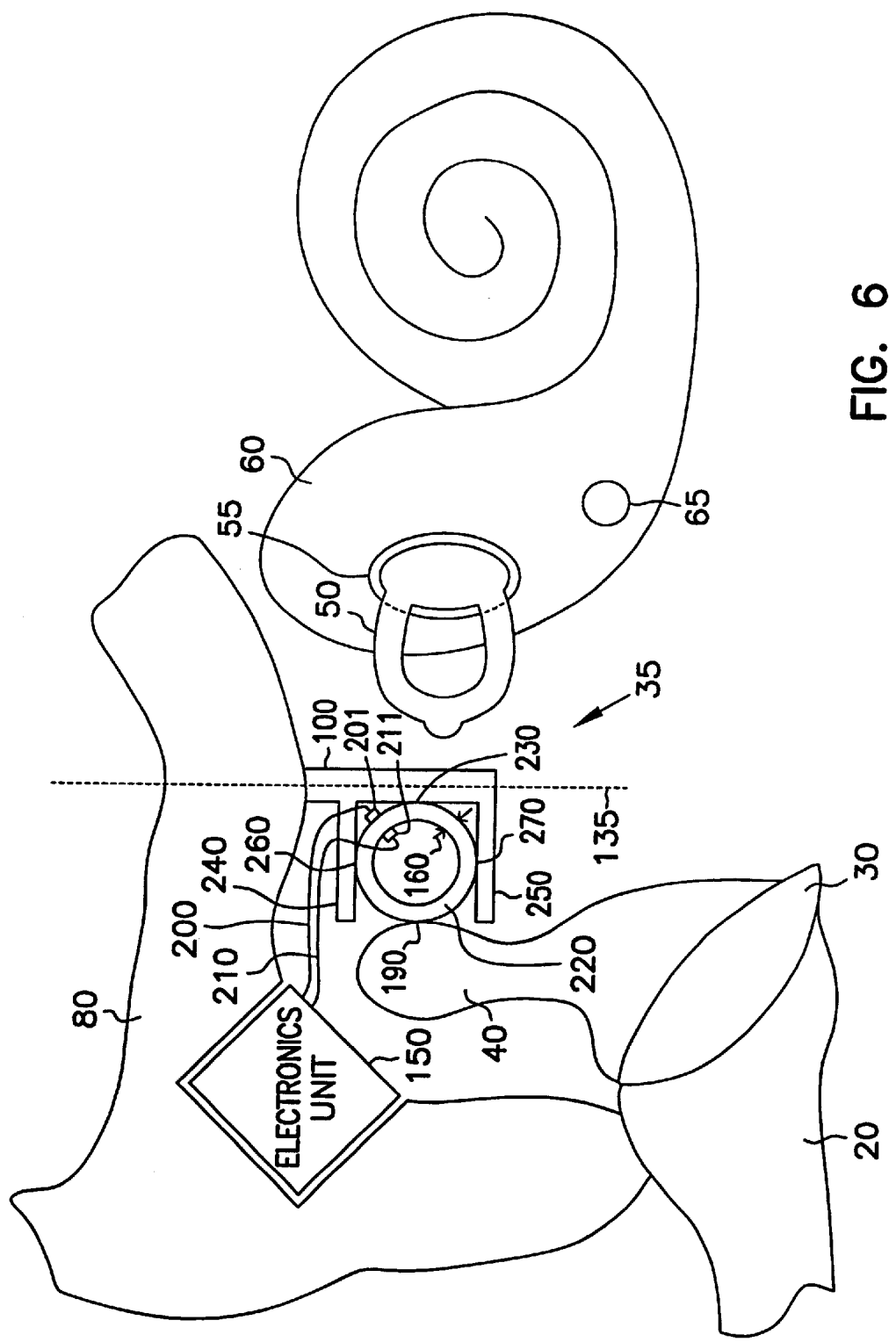
FIG. 6 is a schematic illustration of another embodiment of the invention having a hoop-shaped piezoelectric input transducer film.

FIG. 6 illustrates an electromechanical input transducer embodiment of the invention. Film 220 is interposed between mount 100 and malleus 40. Film 220 is mechanically coupled, and optionally affixed, to malleus 40 to define the location of vibrated point 190, which is intermediate on film 220 between first and second constraint points 260 and 270, or selectably located elsewhere along the circumference of film 220. Sounds received at tympanic membrane 30 cause vibrations in malleus 40, which in turn cause positional variations at a vibrated point 190. The positional variations at vibrated point 190 are typically approximately orthogonal to the longitudinal direction 135 of mount 100. Forces resulting from positional variations in vibrated point 190 impart a stress in the circumferential length of film 220, which in turn produces a resulting electrical output signal across thickness 160 of film 220. The electrical output signal across thickness 160 of film 220 is provided to electronics unit 150 through input leads 200 and 210 electrically coupled to connection points 201 and 211, respectively located across the thickness 160 of the film 220 at any convenient points.

Figure 7:
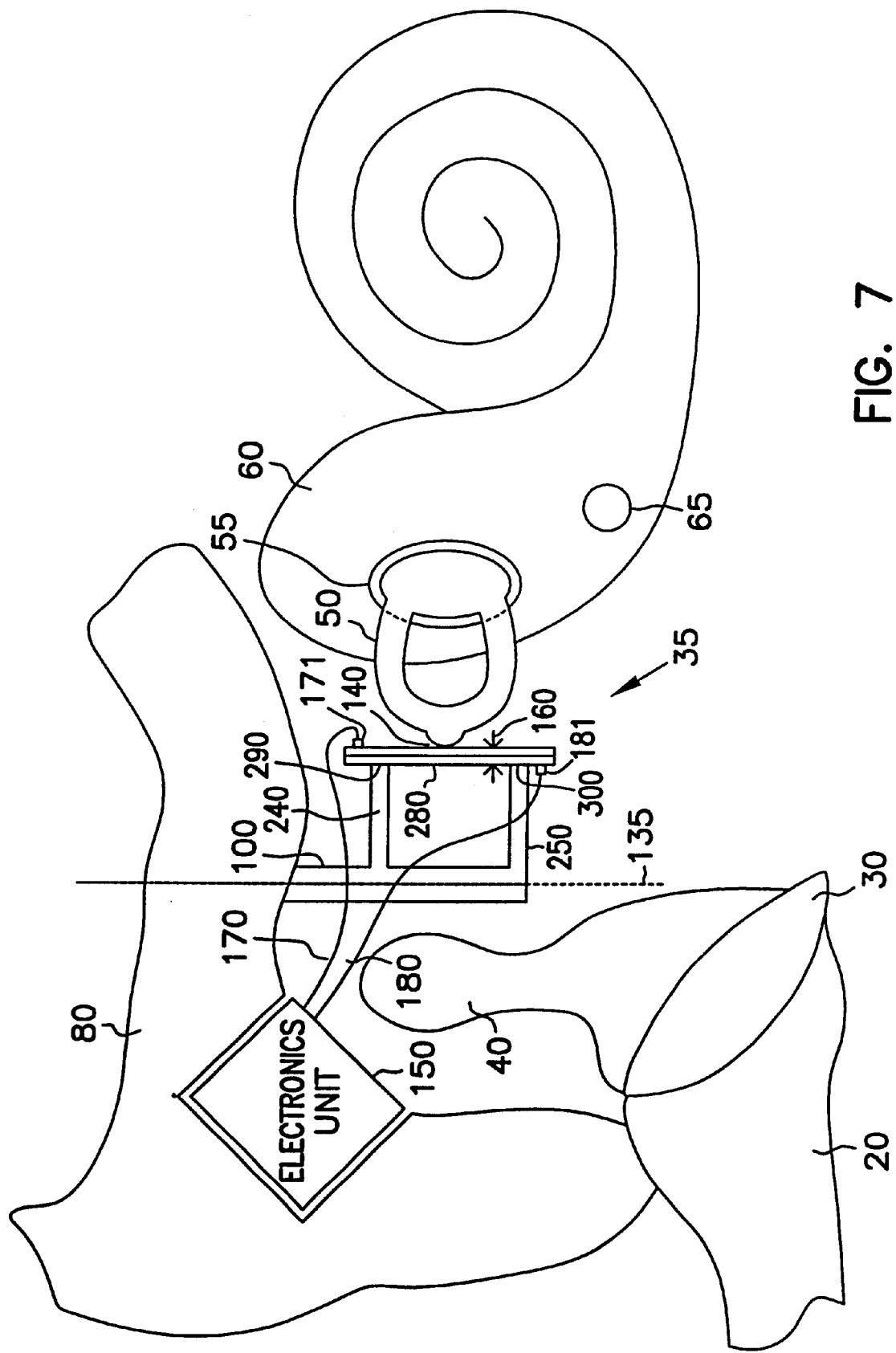
FIG. 7 is a schematic illustration of another embodiment of the invention having a substantially straight piezoelectric output bi-element transducer film.

FIG. 7 illustrates an electromechanical output transducer embodiment of the invention in middle ear 35. Piezoelectric transducer film 280 is, in one embodiment, a bi-element transducer film carried by mount 100. A bi-element transducer film comprises two film elements that are bonded together such that they amplify a piezoelectric action in a direction approximately normal to the bonding plane. Such a bi-element transducer vibrates according to a potential difference applied between two bonded film elements.

Film 280 is interposed between mount 100 and stapes 50. Each element of film 280 comprises the same material described above with respect to film 110. First and second arms 240 and 250 each extend outward radially from mount 100. First and second arms 240 and 250 are mechanically coupled, and preferably secured, to film 280 at respective first and second constraint points 290 and 300. Film 280 is mechanically coupled, and optionally affixed, to stapes 50 to define the location of driving point 140, which is intermediate on film 280 between first and second constraint points 290 and 300, or selectably located elsewhere on film 280.

In FIG. 7, film 280 receives an electrical input signal, representing transduced sounds, from an electronics unit 150 implanted in a cavity of mastoid 80 as part of a MEI hearing system. Electronics unit 150 applies the electrical input signal through its output leads 170 and 180 at connection points 171 and 181, respectively located across the thickness 160 of the film 280 aL any convenient points. Alternating polarities of the applied electrical input signal cause deflections in driving point 140 toward and away from mount 100 when the length of film 280 decreases and increases respectively. The positional variations of driving point 140 are typically approximately orthogonal to the longitudinal direction 135 of mount 100. Forces resulting from the positional variations of driving point 140 are mechanically coupled to stapes 50, causing mechanical vibrations of stapes 50, which are transmitted to cochlea 60 at oval window 55.

Figure 8:
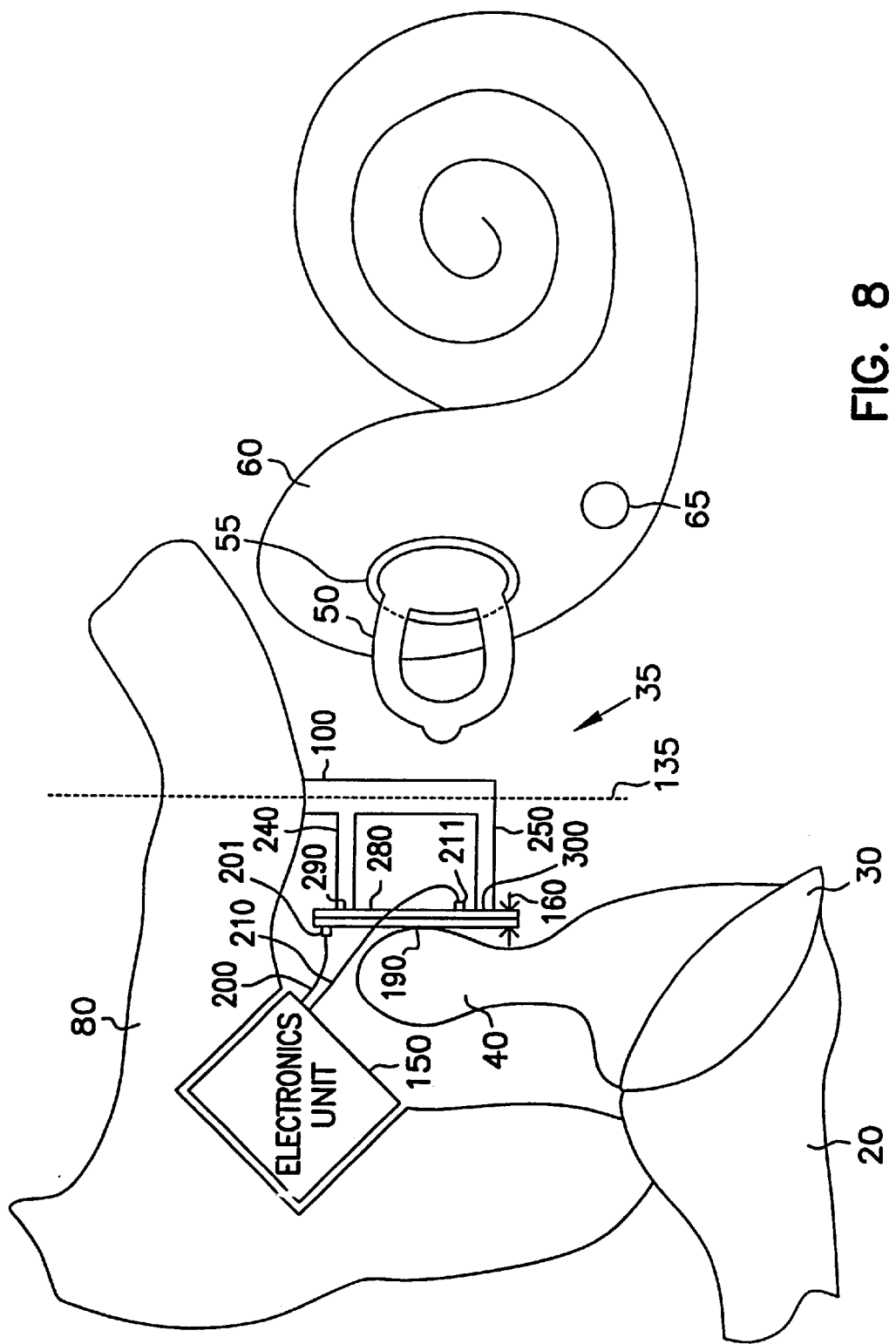
FIG. 8 is a schematic illustration of another embodiment of the invention having a substantially straight piezoelectric input bi-element transducer film.

FIG. 8 illustrates an electromechanical input transducer embodiment of the invention. Film 280 is interposed between mount 100 and malleus 40. Film 280 is, in one embodiment, a bi-element transducer film, as described above. Film 280 is mechanically coupled, and optionally affixed, to malleus 40 to define the location of vibrated point 190, which is intermediate on film 280 between first and second constraint points 290 and 300, or selectably located elsewhere on film 280. Sounds received at tympanic membrane 30 cause vibrations in malleus 40, which in turn cause positional variations at a vibrated point 190. The positional variations at vibrated point 190 are typically approximately orthogonal to the longitudinal direction 135 of mount 100. Forces resulting from positional variations in vibrated point 190 produce a resulting electrical output signal across thickness 160 of film 280. The electrical output signal across thickness 160 of film 280 is provided to electronics unit 150 at its input leads 200 and 210, respectively, across the thickness 160 of the film 280 at any convenient points.

Figure 9:
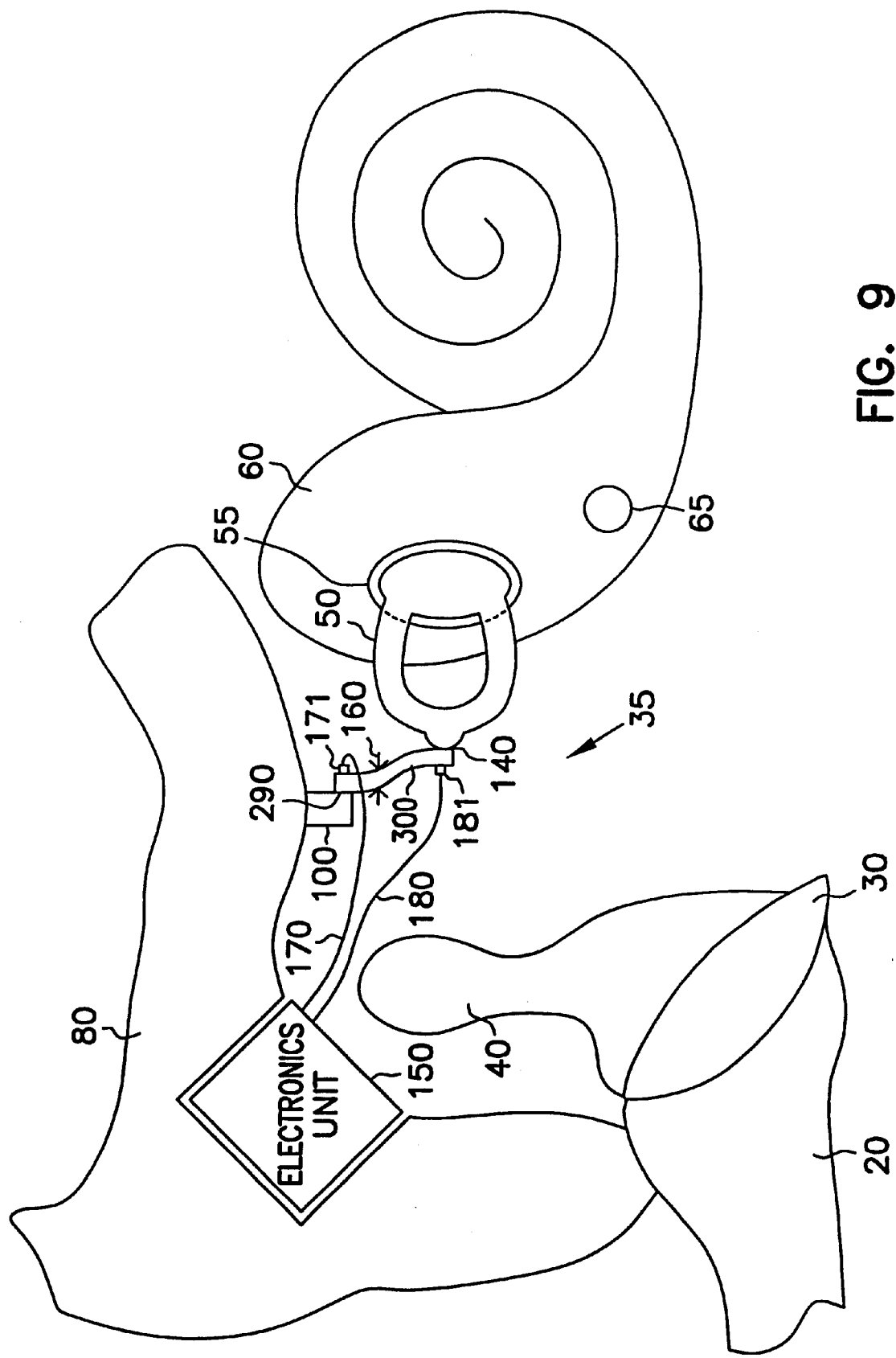
FIG. 9 is a schematic illustration of another embodiment of the invention having a piezoelectric output transducer film, constrained at a mount and at a driving point.

FIG. 9 illustrates an electromechanical output transducer embodiment of the invention in middle ear 35. Piezoelectric transducer film 300 is carried by mount 100. Film 300 comprises the same material described above with respect to film 110. Film 300 is secured to mount 100 at first constraint point 290. Film 300 is mechanically coupled, and optionally affixed, to stapes 50 to define the location of driving point 140, which also serves as a second constraint point.

In FIG. 9, film 300 receives an electrical input signal, representing transduced sounds, from an electronics unit 150 inplanted in a cavity of mastoid 80 as part of a MEI hearing system. Electronics unit 150 applies the electrical input signal through its output leads 170 and 180 at connection points 171 and 181, respectively located across the thickness 160 of the film 300 at any convenient points. Alternating polarities of the applied electrical input signal cause deflections of driving point 140 toward and away from mount 100. Forces resulting from the positional variations of driving point 140 are mechanically coupled to the head portion of stapes 50, causing mechanical vibrations of stapes 50, which are transmitted to cochlea 60 at oval window 55.

Figure 10:
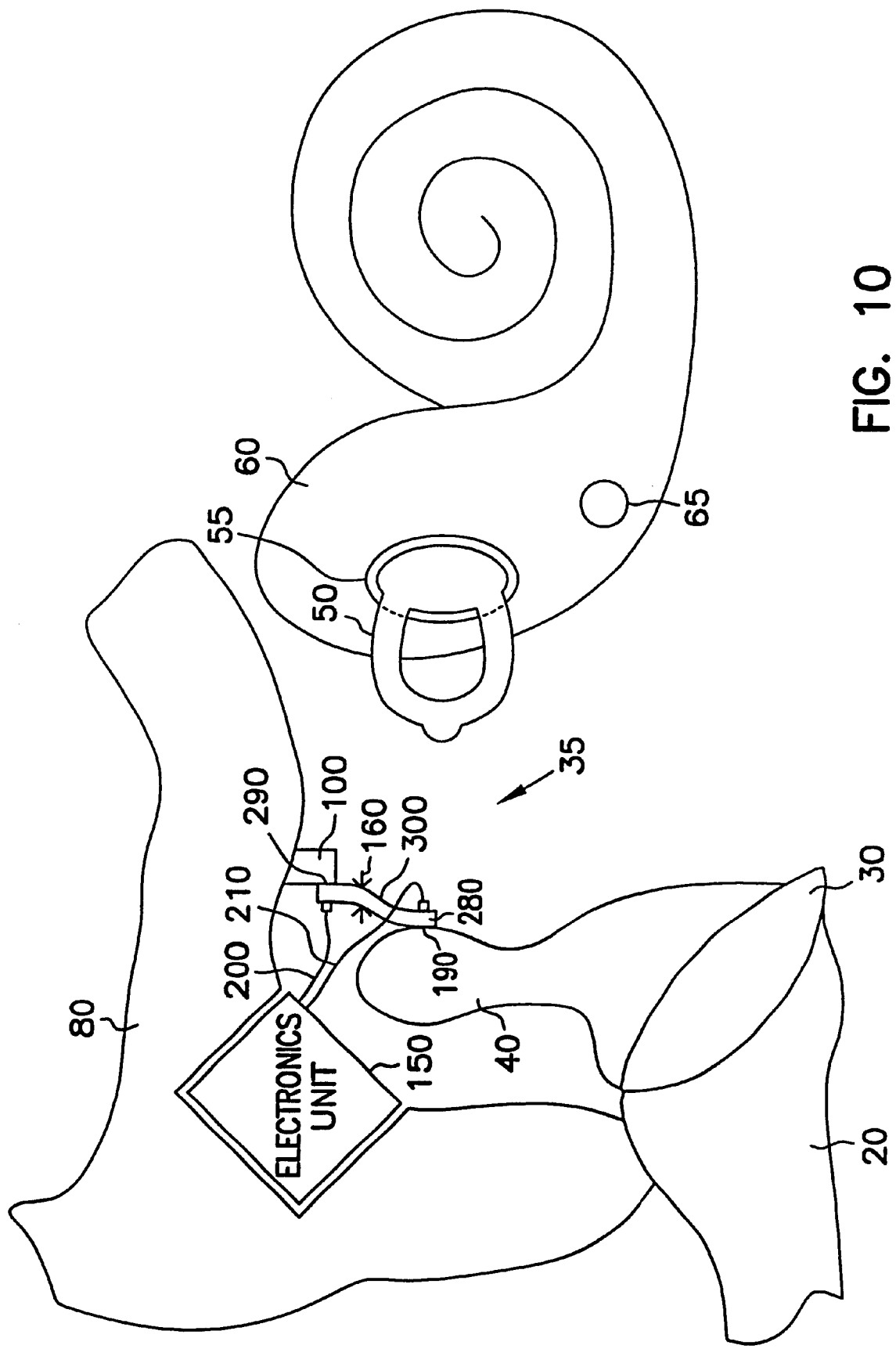
FIG. 10 is a schematic illustration of another embodiment of the invention having a piezoelectric input transducer film, constrained at a mount and at a vibrated point.

FIG. 10 illustrates an electromechanical input transducer embodiment of the invention. Film 300 is secured to mount 100 at first constraint point 290. Film 300 is mechanically coupled, and optionally affixed, to malleus 40 to define the location of vibrated point 190. Sounds received at tympanic membrane 30 cause vibrations in malleus 40, which in turn cause positional variations at a vibrated point 190. The positional variations at vibrated point 190 in turn produces a resulting electrical output signal across thickness 160 of film 300. The electrical output signal across thickness 160 of film 300 is provided to electronics unit 150 through its input leads 200 and 210 at connection points 201 and 211, respectively located across the thickness 160 of the film 300 at any convenient points.

As an input electromechanical transducer in the above described embodiments, mechanical vibrations are typically received from malleus 40. Such vibrations typically have displacements in the range between 1-100 nanometers at audio frequencies and typically average approximately 5 nanometers for 80 dB sound pressure level (SPL) at tympanic membrane 30. As an output electromechanical transducer in the above described embodiments, the invention is capable of producing mechanical vibrations at stapes 50 that include the range of stapedial displacements typically found in a normal auditory system. A sound level of 80 dB SPL at tympanic membrane 30 typically corresponds to a displacement in a range between 0.2 to 2.5 nanometers.

Figure 11:
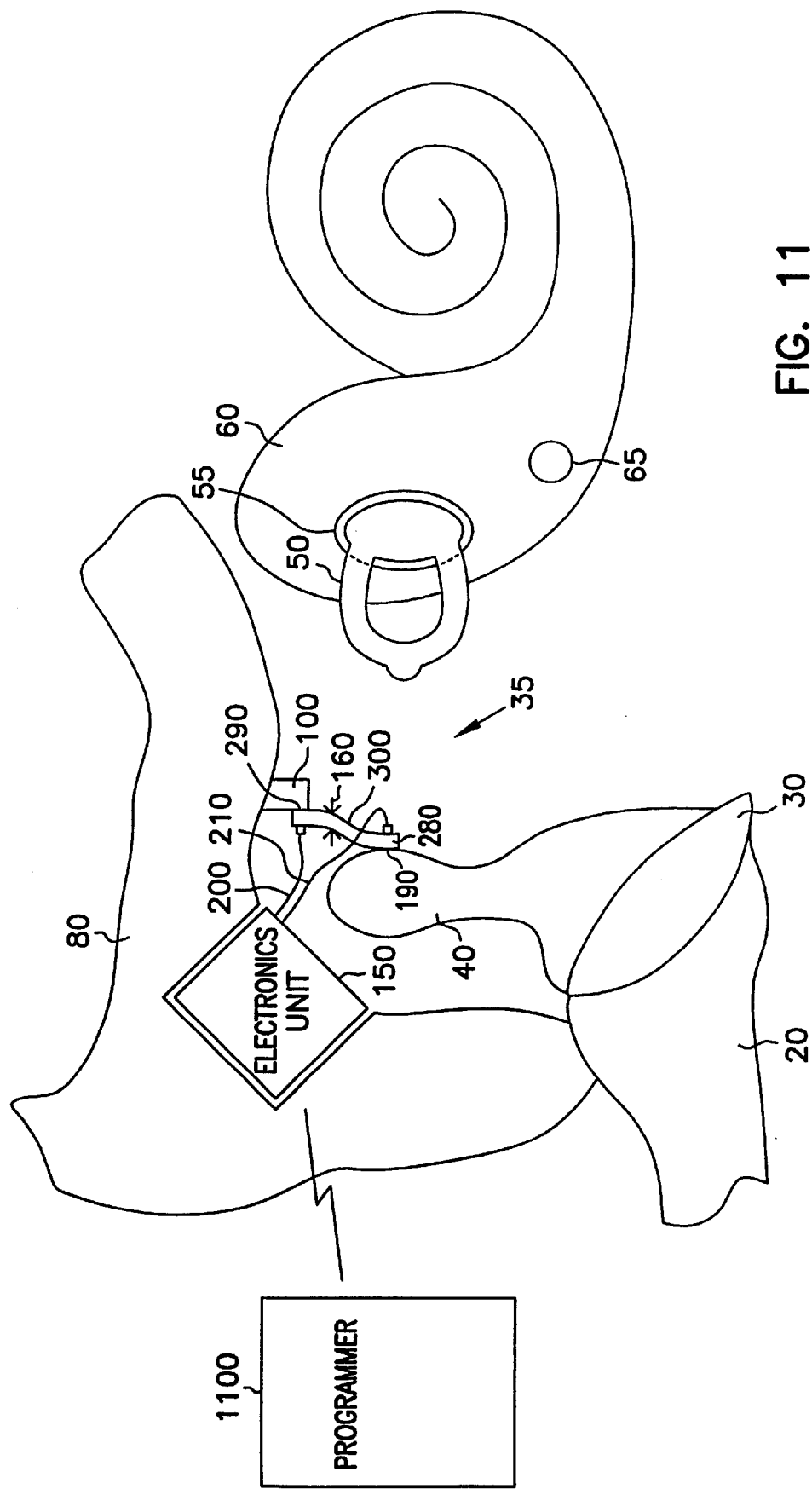
FIG. 11 is a schematic illustration of one embodiment of the invention including an implanted hearing assistance device and an external programmer.

FIG. 11 illustrates an embodiment of the hearing assistance system that also includes an external (i.e., not implanted) programmer 1100, which is communicatively coupled to an external or implantable portion of the hearing assistance device, such as electronics unit 150. Programmer 1100 includes hand-held, desktop, or a combination of hand-held and desktop embodiments, for use by a physician or the patient in which the hearing assistance device is implanted.

In one embodiment, each of programmer 1100 and the hearing assistance device include an inductive element, such as a coil, for inductively-coupled bi-directional transdermal communication between programmer 1100 and the hearing assistance device. Inductive coupling is just one way to communicatively couple programmer 1100 and the hearing assistance device. Any other suitable technique of communicatively coupling programmer 1100 and the hearing assistance device may also be used including, but not limited to, radio-frequency (RF) coupling, infrared (IR) coupling, ultrasonic coupling, and acoustic coupling.

In one embodiment, the signals are encoded using pulse-code modulation (PCM), such as pulse-width telemetry or pulse-interval telemetry. In pulse-width telemetry, communication is by short bursts of a carrier frequency at fixed intervals, wherein the width of the burst indicates the presence of a "1" or a "0". In pulse-interval telemetry, communication is by short fixed-length bursts of a carrier frequency at variable time intervals, wherein the length of the time interval indicates the presence of a "1" or a "0". The data can also be encoded by any other suitable technique, including but not limited to amplitude modulation (AM), frequency modulation (FM), or other communication technique.

The data stream is formatted to indicate that data is being transmitted, where the data should be stored in memory (in the programmer 1100 or the hearing assistance device), and also includes the transmitted data itself. In one embodiment, for example, the data includes an wake-up identifier (e.g., 8 bits), followed by an address (e.g., 6 bits) indicating where the data should be stored in memory, followed by the data itself.

In one embodiment, such communication includes programming of the hearing assistance device by programmer 1100 for adjusting hearing assistance parameters in the hearing assistance device, and also provides data transmission from the hearing assistance device to programmer 1100, such as for parameter verification or diagnostic purposes. Programmable parameters include but are not limited to: on/off, standby mode, type of noise filtering for a particular sound environment, frequency response, volume, gain range, maximum power output, delivery of a test stimulus on command, and any other adjustable parameter. In one embodiment, certain ones of the programmable parameters (e.g., on/off, volume) are programmable by the patient, while others of the programmable parameters (e.g., gain range, filter frequency responses, maximum power output, etc.) are programmable only by the physician.

Though the drawings illustrate the invention coupled to the malleus 40 when used as an input electromechanical transducer and coupled to the stapes 50 when used as an output electromechanical transducer, the invention may also be coupled to other auditory elements within the middle ear 35. Also, incus 45 need not be removed. For example, the invention may also be coupled to receive mechanical vibrations from the tympanic membrane 30 or the malleus 40. In another example, the invention may also be coupled to vibrate incus 45, oval window 55, round window 65, vestibule 61, or semicircular canals 62.

For clarity, the above described embodiments have been described with respect to function as either electromechanical input or output transducers. The piezoelectric effect allows both mechanical-to-electrical and electrical-to-mechanical transducing. Accordingly, each of the above described embodiments are intended to function as either electromechanical input transducers for sensing mechanical vibrations, or as electromechanical output transducers for producing mechanical vibrations. In particular, the above described embodiments may be switched between vibrating and vibrated auditory elements to obtain the desired functionality, and electrical signals can be accordingly coupled to an electronics unit of either a P-MEI or T-MEI hearing aid, or other at least partially implantable hearing system such as a cochlear implant with middle ear vibration sensing. Also, inventive concepts illustrated in particular embodiments are intended to also apply to the other embodiments disclosed herein.

By utilizing the piezoelectric films described above, the invention provides several advantages over ceramic piezoelectric transducers sometimes used in MEI hearing systems. PVDF films offer a relatively flat frequency response over a wide frequency range. PVDF films are particularly desirable as input electromechanical transducers for sensing mechanical vibrations since they provide a higher voltage output in response to an applied force input than a piezoelectric ceramic material. PVDF films also have a high elastic compliance, which allows malleus 40 to vibrate more freely when coupled at vibrated point 190 to a piezoelectric film transducer than when coupled to a piezoelectric ceramic transducer material.

Thus, the invention provides a method and apparatus for transducing between mechanical and electrical signals within a middle ear to improve hearing using a piezoelectric transducer film in conjunction with an electronics unit of an implantable hearing system such as a partial middle ear implantable (P-MEI) or total middle ear implantable (T-MEI) hearing system.

What is claimed is:

1. A method of assisting hearing including:
    mechanically coupling a piezoelectric transducer film, carried by a mount, to an auditory element of a middle ear and securing the film within the middle ear;
    receiving vibrations from the auditory element with the film and producing a resulting output voltage in response to the vibrations; and
    sending the output voltage from the film to an electronics unit coupled to the film and communicatively coupling the electronics unit to a programmer.

2. The method of claim 1, in which the step of mechanical coupling further comprises using at least one of a bow shape transducer film, a hoop shape transducer film, and a substantially straight shape transducer film.

3. The method of claim 1, in which the step of mechanical coupling further comprises securing the film at a plurality of constraint points.

4. The method of claim 1, in which the step of mechanical coupling further comprises using film made of polyvinylidene fluoride.

5. The method of claim 1, in which the step of mechanical coupling further comprises transforming vibrations of the auditory element with the film into longitudinal dimensional variations of the film.

6. The method of claim 1, in which the step of mechanical coupling further comprises using a bi-element transducer film.

7. The method of claim 1, in which the step of mechanical coupling further comprises extending first and second arms radially outward from the mount and mechanically coupling the first and second arms to the film.

8. A method of assisting hearing comprising:
    mechanically coupling a piezoelectric transducer film, carried by a mount, to an auditory element of a middle ear and securing the film at a plurality of constraint points within the middle ear;
    sending an electrical input signal from an electronics unit to the film and communicatively coupling the electronics unit to a programmer; and
    vibrating the auditory element with the film in response to the electrical input signal.

9. The method of claim 8, in which the step of mechanical coupling further comprises using at least one of a bow shape transducer film, a hoop shape transducer film, and a substantially straight shape transducer film.

10. The method of claim 8, in which the step of mechanical coupling further comprises using film made of polyvinylidene fluoride.

11. The method of claim 8, in which the step of mechanical coupling further comprises transforming vibrations of the auditory element with the film into longitudinal dimensional variations of the film.

12. The method of claim 8, in which the step of mechanical coupling further comprises using a bi-element transducer film.

13. The method of claim 8, in which the step of mechanical coupling further comprises extending first and second arms radially outward from the mount and mechanically coupling the first and second arms to the film.

14. A method of assisting hearing comprising:
    mechanically coupling a piezoelectric transducer film, carried by a mount, to an auditory element of an inner ear and securing the film at a plurality of constraint points within the middle ear;
    sending a electrical input signal from an electronics unit to the film and communicatively coupling the electronics unit to a programmer; and
    vibrating the auditory element with the film in response to the electrical input signal.

15. The method of claim 14, in which the step of mechanical coupling further comprises coupling the film to at least one of an oval window, a round window, a vestibule, and a semicircular canal of the inner ear.

16. An at least partially implantable hearing assistance system, comprising:
    an electromechanical sensor, including a mount adapted to be secured to a middle ear, and a piezoelectric transducer film carried by the mount, in which the film is proportioned for mechanically coupling to an auditory element in the middle ear, and the film is adapted for receiving vibrations from the auditory element and producing a resulting output voltage in response to the vibrations, the film having at least one of a hoop shape, a substantially straight shape, and a bow shape;
    an electronics unit, electrically coupled to said sensor for receiving said output voltage; and a programmer, adapted for communicative coupling to the electronics unit.

17. An at least partially implantable hearing assistance system, comprising:

a vibrator including a mount, adapted to be secured to a middle ear and a piezoelectric transducer film, carried by the mount, proportioned to be mechanically coupled to the middle ear and to vibrate an auditory element in response to an electrical input signal, the film being adapted to be secured at a plurality of constraint points and having at least one of a hoop shape, a substantially straight shape, and a bow shape;

an electronics unit, electrically coupled for providing the electrical input signal to the vibrator; and a programmer, adapted for communicative coupling to the electronics unit.

18. An at least partially implantable hearing assistance system, comprising:

a vibrator including a mount, adapted to be secured to a middle ear and a piezoelectric transducer film, carried by the mount, the film being secured to transform longitudinal variations in a physical dimension of the film into vibrations of the auditory clement and proportioned to be mechanically coupled to the middle ear and to vibrate the auditory element in response to an electrical input signal;

an electronics unit, electrically coupled for providing the electrical input signal to the vibrator; and a programmer, adapted for communicative coupling to the electronics unit.

19. An at least partially implantable hearing assistance system, comprising:

a vibrator including a mount, adapted to be secured to a middle ear and a piezoelectric transducer film, carried by the mount, the film having a hoop shape and proportioned to be mechanically coupled to the middle ear and to vibrate the auditory element in response to an electrical input signal;

an electronics unit, electrically coupled for providing the electrical input signal to the vibrator; and a programmer, adapted for communicative coupling to the electronics unit.

20. An at least partially implantable hearing assistance system, comprising:

a vibrator including a mount, adapted to be secured to a middle ear and a piezoelectric transducer film, carried by the mount, the film having a bow shape and proportioned to be mechanically coupled to the middle ear and to vibrate the auditory element in response to an electrical input signal;

an electronics unit, electrically coupled for providing the electrical input signal to the vibrator; and a programmer, adapted for communicative coupling to the electronics unit.

21. An at least partially implantable hearing assistance system, comprising:

a vibrator including a mount, adapted to be secured to a middle ear and a piezoelectric transducer film, carried by first and second arms, each extending radially outward from the mount and mechanically coupled to the film, the film being proportioned to be mechanically coupled to the middle ear and to vibrate the auditory element in response to an electrical input signal;

an electronics unit, electrically coupled for providing the electrical input signal to the vibrator; and a programmer, adapted for communicative coupling to the electronics unit.

22. An at least partially implantable hearing assistance system, comprising:

a vibrator including a mount, adapted to be secured to a middle ear and a piezoelectric transducer film, and the mount is mechanically coupled to the film at first and second constraint points, and having between the first and second constraint points at least one driving point on the film coupled to an auditory element at the driving point such that a variation in the film length between the first and second constraint points is transformed into an approximately orthogonal variation in position of the driving point for vibrating the auditory element, the film being proportioned to be mechanically coupled to the middle ear and to vibrate the auditory element in response to an electrical input signal;

an electronics unit, electrically coupled for providing the electrical input signal to the vibrator; and a programmer, adapted for communicative coupling to the electronics unit.

23. An at least partially implantable hearing assistance system, comprising:

a vibrator including a mount, adapted to be secured to a middle ear and a piezoelectric transducer film, carried by the mount, the film being secured at a plurality of constraint points and proportioned to be mechanically coupled to an auditory element of an inner ear and to vibrate the auditory clement in response to an electrical input signal, the film being adapted to be secured at a plurality of constraint points;

an electronics unit, electrically coupled for providing the electrical input signal to the vibrator; and a programmer, adapted for communicative coupling to the electronics unit.

24. An at least partially implantable hearing assistance systems, comprising:

a vibrator including a mount, adapted to be secured to a middle ear and a piezoelectric transducer film, carried by the mount, the film being secured to transform longitudinal variations in a physical dimension of the film into vibrations of the auditory element and proportioned to be mechanically coupled to an auditory element of an inner ear and to vibrate the auditory element in response to an electrical input signal, the film being adapted to be secured at a plurality of constraint points;

an electronics unit, electrically coupled for providing the electrical input signal to the vibrator; and a programmer, adapted for communicative coupling to the electronics unit.

25. An at least partially implantable hearing assistance system, comprising:

a vibrator including a mounts adapted to be secured to a middle ear and a piezoelectric transducer film, carried by first and second arms, each extending radially outward from the mount and mechanically coupled to the film, the film being proportioned to be mechanically coupled to an auditory element of an inner car and to vibrate the auditory element in response to an electrical input signal, the film being adapted to be secured at a plurality of constraint points;

an electronics unit, electrically coupled for providing the electrical input signal to the vibrator; and a programmer, adapted for communicative coupling to the electronics unit.

26. An at least partially implantable hearing assistance system, comprising:
  a vibrator including a mount, adapted to be secured to a middle ear and a piezoelectric transducer film, carried by first and second arms, each extending radially outward from the mount and mechanically coupled to the film at first and second constraint points, and having between the first and second constraint points at least one driving point on the film coupled to an auditory element at the driving point such that a variation in the film length between the first and second constraint points is transformed into an approximately orthogonal variation in position of the driving point for vibrating the auditory element, the film being proportioned to be mechanically coupled to an auditory element of all inner ear and to vibrate the auditory clement in response to an electrical input signal, the film being adapted to be secured at a plurality of constraint points;
  an electronics unit, electrically coupled for providing the electrical input signal to the vibrator; and
  a programmer, adapted for communicative coupling to the electronics unit.

27. An at least partially implantable hearing assistance system, comprising:
  a vibrator including a mount and a piezoelectric transducer film, the mount being securable proximate a patient's middle ear and the piezoelectric transducer film being carried by the mount and conformed to be mechanically coupled to the middle ear such that an auditory element is vibrated in response to an electrical input signal;
  an electronics unit in electrical communication with the vibrator and providing the electrical input signal to the vibrator; and
  a programmer adapted for inductive communicative coupling to the electronics unit.

28. An at least partially implantable hearing assistance system, comprising:
  a vibrator including a mount and a piezoelectric transducer film, the mount being securable proximate a patient's middle car and the piezoelectric transducer film being carried by the mount and conformed to be mechanically coupled to the middle ear such that all auditory element is vibrated in response to an electrical input signal;
  an electronics unit in electrical communication with the vibrator and providing the electrical input signal to the vibrator; and
  a programmer adapted for radio-frequency communicative coupling to the electronics unit.

29. An at least partially implantable hearing assistance system, comprising:
  a vibrator including a mount and a piezoelectric transducer film, the mount being securable proximate a patient's middle ear and the piezoelectric transducer film being carried by the mount and conformed to be mechanically coupled to the middle ear such that an auditory element is vibrated in response to an electrical input signal;
  an electronics unit in electrical communication with the vibrator and providing the electrical input signal to the vibrator; and
  a programmer adapted for infrared communicative coupling to the electronics unit.

30. An at least partially implantable hearing assistance system, comprising:
  a vibrator including a mount and a piezoelectric transducer film, the mount being securable proximate a patient's middle ear and the piezoelectric transducer film being carried by the mount and conformed to be mechanically coupled to the middle ear such that an auditory element is vibrated in response to an electrical input signal;
  an electronics unit in electrical communication with the vibrator and providing the electrical input signal to the vibrator; and
  a programmer adapted for ultrasonic communicative coupling to the electronics unit.

31. An at least partially implantable hearing assistance system, comprising:
  a vibrator including a mount and a piezoelectric transducer film, the mount being securable proximate a patient's middle ear and the piezoelectric transducer film being carried by the mount and conformed to be mechanically coupled to the middle ear such that an auditory element is vibrated in response to an electrical input signal;
  an electronics unit including in inductive element an electrical communication with the vibrator and providing the electrical input signal to the vibrator; and
  a programmer including an inductive clement adapted for inductive communicative coupling to the electronics unit.

32. The system of claim 31, in which the inductive clement is a coil.

33. An at least partially implantable hearing assistance system, comprising:
  a vibrator Including a mount and a piezoelectric transducer film, the mount being securable proximate a patient's middle ear and the piezoelectric transducer film being carried by the mount and conformed to be mechanically coupled to the middle car such that an auditory element is vibrated in response to an electrical input signal;
  an electronics unit in electrical communication with the vibrator and providing the electrical input signal to the vibrator; and
  a programmer adapted for communicative coupling to the electronics unit, including means for pulse-code modulation, said means for pulse-code modulation encoding signals to said electronics unit.

34. The programmer of claim 33, in which the pulse-code modulating means are bi-directional between the programmer and the electronics unit.

35. The programmer of claim 33, in which the pulse-code modulating means comprises pulse-width telemetry.

36. The programmer of claim 33, in which the pulse-code modulating means comprises pulse-interval telemetry.

37. The programmer of claim 33, in which the pulse-code modulating means comprises amplitude modulation.

38. The programmer of claim 37, in which the pulse-code modulating means comprises frequency modulation.

39. An at least partially implantable hearing assistance system, comprising:
  a vibrator including a mount and a piezoelectric transducer film, the mount being securable proximate a patient's middle ear and the piezoelectric transducer film being carried by the mount and conformed to be mechanically coupled to the middle ear such that an auditory element is vibrated in response to an electrical input signal;

an electronics unit in electrical communication with the vibrator and providing the electrical input signal to the vibrator; and a programmer adapted for communicative coupling to the electronics unit, including means for adjusting bearing assistance parameters and means for hearing assistance parameter verification.

40. An at least partially implantable hearing assistance system, comprising:

a vibrator including a mount and a piezoelectric transducer film, the mount being securable proximate a patient's middle ear and the piezoelectric transducer film being carried by the mount and conformed to be mechanically coupled to the middle ear such that an auditory element is vibrated in response to an electrical input signal;

an electronics unit in electrical communication with the vibrator and providing the electrical input signal to the vibrator; and a programmer adapted for communicative coupling to the electronics unit, including means for adjusting hearing assistance parameters and means for hearing assistance parameter diagnostics.

41. A method of programming a hearing assistance system at least partially implanted in a patient's middle car, the method comprising the steps of:

activating a programmer adapted for communicative coupling to an electronics unit, the electronics unit being disposed proximate the patient's middle ear and in electrical contact with a vibrator, the vibrator including a mount and a piezoelectric transducer film, the mount secured proximate the patient's middle ear and the transducer film being carried by the mount and proportioned to be mechanically coupled to the patient's middle ear;

setting a value of a hearing assistance parameter in the programmer; and transdermally communicating, the hearing assistance parameter value from the programmer to the electronics unit, at least in part by induction.

42. A method of programming a hearing assistance system at least partially implanted in a patient's middle ear, the method comprising the steps of:

activating a programmer adapted for communicative coupling to an electronics unit, the electronics limit being disposed proximate the patient's middle ear and in electrical contact with a vibrator, the vibrator including a mount and a piezoelectric transducer film, the mount secured proximate the patient's middle ear and the transducer film being carried by the mount and proportioned to be mechanically coupled to the patient's middle ear;

setting a value of a hearing assistance parameter in the programmer; and transdermally communicating the hearing assistance parameter value from the programmer to the electronics unit, at least in part by radio frequency.

43. A method of programming a hearing assistance system at least partially implanted in a patient's middle ear, the method comprising the steps of:

activating a programmer adapted for communicative coupling to an electronics unit, the electronics unit being disposed proximate the patient's middle ear and in electrical contact with a vibrator, the vibrator including a mount and a piezoelectric transducer film, the mount secured proximate the patient's middle ear and the transducer film being carried by the mount and proportioned to be mechanically coupled to the patient's middle ear;

setting a value of a hearing assistance parameter in the programmer; and transdermally communicating the hearing assistance parameter value from the programmer to the electronics unit, at least in part by infrared radiation or ultrasonic radiation.

* * * * *